United States Patent [19]

Shannon

[11] 4,059,106

[45] Nov. 22, 1977

[54] EAR RACK FOR VETERINARY PURPOSES

[76] Inventor: Richard D. Shannon, 10510 Barnhart Court, Cupertino, Calif. 95014

[21] Appl. No.: 711,737

[22] Filed: Aug. 5, 1976

[51] Int. Cl.[2] .......... A61F 13/00

[52] U.S. Cl. .......... 128/133; 119/143; 128/346

[58] Field of Search .......... 128/132–135, 128/346, 76 R; 119/106, 143

[56] References Cited

U.S. PATENT DOCUMENTS

| | | | |
|---|---|---|---|
| 669,909 | 3/1901 | Young | 119/143 |
| 2,509,441 | 5/1950 | MacAllan | 128/346 |
| 2,587,966 | 3/1952 | Cleary | 128/346 |
| 3,257,990 | 6/1966 | Robertson et al. | 119/143 X |

*Primary Examiner*—Lawrence W. Trapp
*Attorney, Agent, or Firm*—David A. Boone

[57] ABSTRACT

An ear rack comprises a rigid frame coupled to a flexible base which is adapted for encircling an animal's head. The flexible base includes a strap-like portion which has perforations therethrough for engaging with a latching mechanism. The latching mechanism allows a predetermined amount of movement in the strap to provide for the maximum comfort of the animal by accommodating such animal movements as jaw movements during eating.

5 Claims, 6 Drawing Figures

EAR RACK FOR VETERINARY PURPOSES

BACKGROUND AND SUMMARY OF THE INVENTION

Ear racks are used by veterinarians to position the ears of dogs and other animals after operations such as cropping to ensure proper healing and, in the case of cropping operations, to ensure the cropped ears will assume the desired shape and position. Previous ear racks have been makeshift arrangements using stiff wire (such as that used in coat hangers) and large amounts of tape (typically bandage adhesive tape) to affix the animal's ears to the rigid frame and the frame to the animal's head. These prior art units have had the disadvantage that they worked loose and disengaged from the dog's head due to the movements of the animal.

In accordance with the preferred embodiment of the present invention, an ear rack is provided which comprises a rigid frame with a flexible base having a strap-like portion for insertion of the animal's head. The strap-like portion has perforations which engage a latching mechanism. This latching mechanism allows a predetermined amount of movement in the positioning of the strap while it is in the latched condition. This provides the maximum of comfort to the animal wearing the ear rack by allowing some play in the strap. Since the animal is not as irritated during eating, etc., he is less likely to attempt to forcibly remove the rack. Also, the latch is designed to disengage under a predetermined amount of stress on the strap. Therefore, if by chance the ear rack should catch on some object, the violent tugging of the animal causes the latch to disengage and release the animal.

DESCRIPTION OF THE PREFERRED EMBODIMENT

Figure 1:
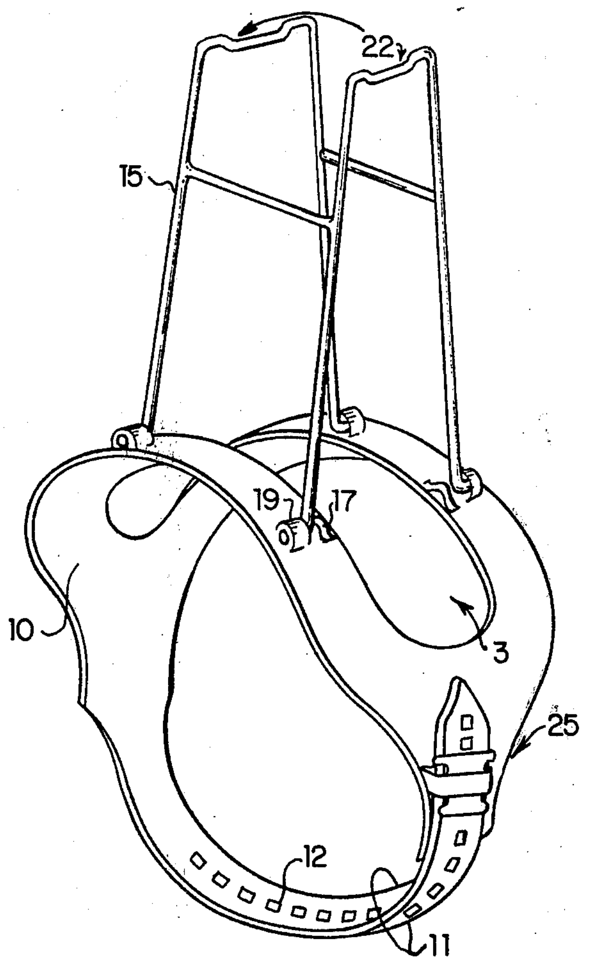
FIG. 1 is an ear rack in accordance with the preferred embodiment.
Figure 2:
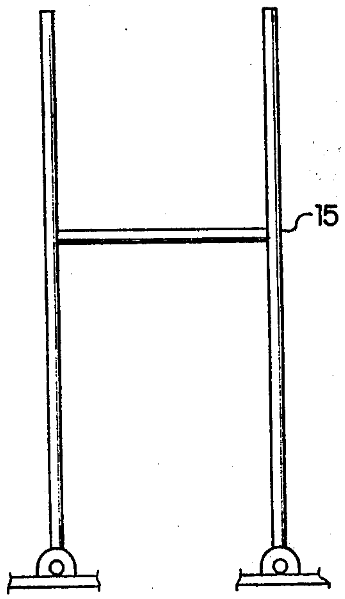
FIG. 2 is a front view and FIG. 3 is a side view of the rigid frame used in the ear rack of the preferred embodiment.

Referring to FIG. 1, there is shown a perspective view of an ear rack in accordance with the preferred embodiment. Some particular ornamental design features of this ear rack are the subject of the applicant's co-pending patent application Ser. No. 601,227, filed on Aug. 1, 1975, and entitled "Veterinary Ear Rack."

Flexible base 10 comprises a plastic material such as low density polyethylene, which can provide a firm but flexible base to support rigid frame 15. Strap-like portion 11 has a series of perforations 12 therethrough. A latching mechanism 25, more fully described below, is provided to engage these perforations and hold the strap in place. When the ear rack 10 is in position over the animal's head, the ears of the animal will be extending through opening 3. The ears are then affixed to the frame through the use of adhesive tape. Indentations 22 in rigid frame 15 are provided to facilitate the fastening of the adhesive tape to the frame. Note that these indentations 22 prevent the tape from slipping off the top of the frame.

Figure 3:
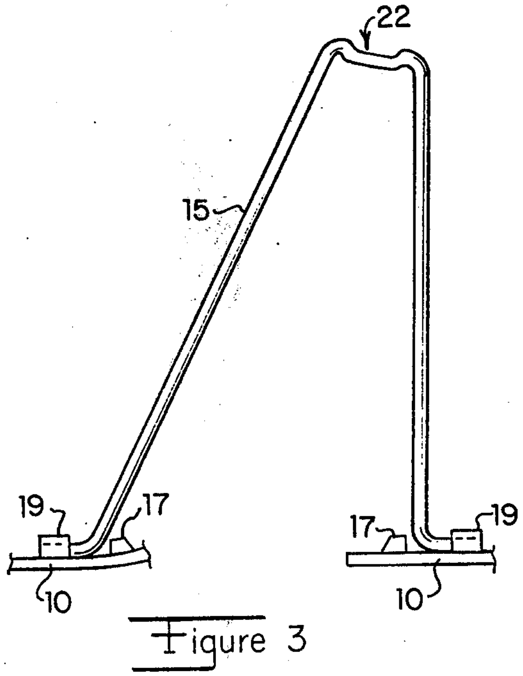

Rigid frame 15 is held securely in place on base 10 by projections 19 and 17. This is more clearly shown in FIG. 3. The ends of rigid frame 15 are inserted through openings in projections 19. To facilitate this insertion, the flexible frame 10 is bent to move projections 17 from blocking the entry of the ends of frame 15. Once inserted, flexible base 10 is released and projections 17 assume the normal position as shown in FIG. 3. Thus, rigid frame 15 will be held firmly in place on base 10.

Figure 5:
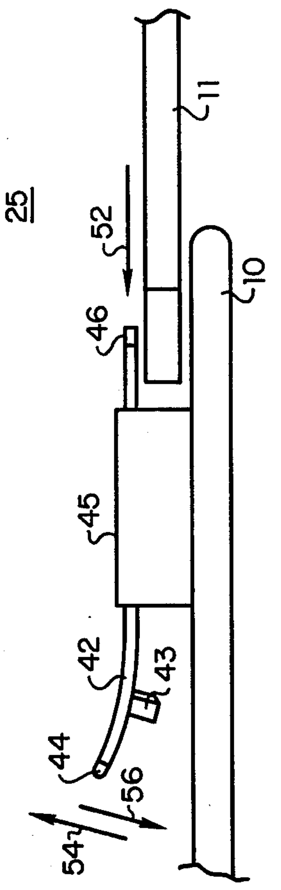
FIGS. 5 and 6 are side views of the strap and latching mechanism of the preferred embodiment.
Figure 6:
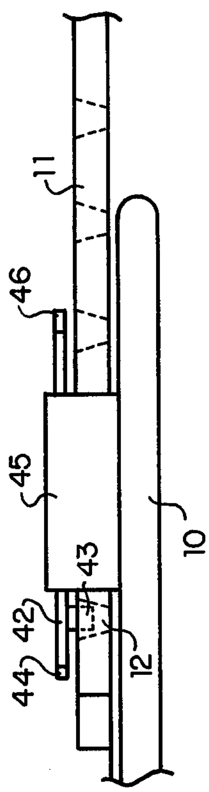
Figure 4:
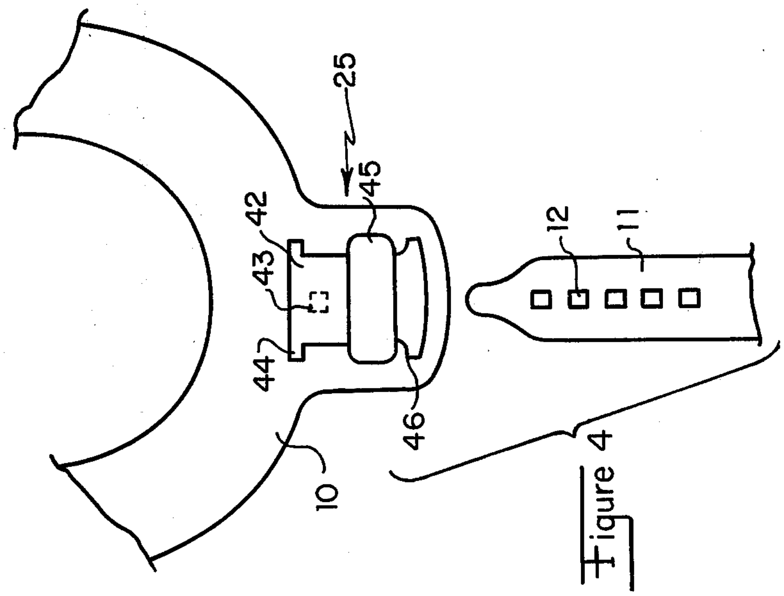
FIG. 4 is a top view of the strap and latching mechanism of the preferred embodiment.

Referring now to FIGS. 4, 5 and 6, there is shown the latching mechanism used in the preferred embodiment. Member 45 extends outward from base 10 forming an opening through which member 42 is positioned. Member 42 can move freely back and forth in an opening formed by member 45, but it cannot be easily removed because of T-like projections 44 and 46. Extending out from member 42 is a projection 43. This projection is designed to engage with the perforations 12 in strap-like portion 11, i.e., as strap 11 is inserted through the opening formed by member 45, projection 43 will lodge in one of the perforations 12 and thereby hold strap-like portion 11 in the latched position. Note, however, that strap-like portion 11 is not held at a single fixed point. After projection 43 engages with one of perforations 12, member 42 and strap-like portion 11 may still move together through the opening formed by member 45, limited in their travel only by key-like projections 44 and 46. Therefore, a predetermined amount of travel in the strap after latching is provided by varying the distance between T-like projections 44 and 46. Of course, there is less and less travel as the distance between key-like projections 44 and 46 approaches the width of member 45.

Strap-like portion 11 may be disengaged from member 42 by lifting member 42 up in the direction shown by arrow 54 in FIG. 5. Depending on the amount of spring in the material used for member 42, member 42 may spring back into position to engage the perforations 12 or it may be pushed down in the direction shown by arrow 56 to engage the perforations in strap-like member 11.

In FIG. 6, member 42 is shown latched to strap-like portion 11. Note that in the preferred embodiment projection 43 is designed so as not to extend fully through perforation 12. In addition, the edges of perforation 12 are slightly chamfered. In this way, i.e., by varying the height of projection 43 and the chamfer on projections 12, the latch can be made to disengage when a predetermined amount of force is applied to strap-like portion 11.

I claim:

1. A veterinary apparatus for use in supporting the ears of an animal, said apparatus comprising:

a flexible base having a strap-like portion extending therefrom;

a rigid frame coupled to the flexible base for coupling to the animal's ears;

latching means coupled to said base for engaging said strap-like portion and for resisting disengagement therewith; and means coupled to said latching means for allowing a predetermined amount of movement of said strap-like portion when it is engaged with said latching means.

2. Veterinary apparatus as in claim 1 wherein said strap-like portion has perforations of a first shape extending therefrom, and said latching means comprises:

a first member coupled to said base for defining an opening between said first member and said base;

a second member, having a projection extending therefrom, said second member extending through either side of said opening a predetermined distance and having portions on either end thereof for causing the second member to remain captively positioned through said opening, said perforations in said strap-like portion being disposed to engage with said projection when said strap-like portion is inserted through said opening.

3. Veterinary apparatus as in claim 1 and further comprising release means coupled to the latching means for causing said latching means to disengage from said strap-like portion when a predetermined amount of force is applied thereto.

4. Veterinary apparatus as in claim 3 wherein said rigid frame is coated with a resilient material.

5. Apparatus as in claim 4 wherein said rigid frame includes indentations for facilitating the fastening of tape thereto.

* * * * *